United States Patent
Serban et al.

(10) Patent No.: US 10,981,149 B2
(45) Date of Patent: Apr. 20, 2021

(54) DEHYDROGENATION CATALYST WITH OPTIMUM MODIFIER PROFILE INDEX

(71) Applicant: UOP LLC, Des Plaines, IL (US)

(72) Inventors: Manuela Serban, Northbrook, IL (US); Matthew C. Cole, Evanston, IL (US); Clayton C. Sadler, Arlington Heights, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 16/817,184

(22) Filed: Mar. 12, 2020

(65) Prior Publication Data

US 2020/0298213 A1    Sep. 24, 2020

Related U.S. Application Data

(60) Provisional application No. 62/820,117, filed on Mar. 18, 2019.

(51) Int. Cl.
| | | |
|---|---|---|
| *B01J 23/00* | (2006.01) | |
| *B01J 23/62* | (2006.01) | |
| *B01J 35/08* | (2006.01) | |
| *C07C 5/333* | (2006.01) | |

(52) U.S. Cl.
CPC .......... *B01J 23/626* (2013.01); *B01J 35/08* (2013.01); *C07C 5/3337* (2013.01); *C07C 2523/04* (2013.01); *C07C 2523/14* (2013.01); *C07C 2523/42* (2013.01); *C07C 2523/58* (2013.01); *C07C 2523/62* (2013.01)

(58) Field of Classification Search
CPC ... C07C 5/3337; C07C 11/09; C07C 2523/04; C07C 2523/14; C07C 2523/42; C07C 2523/58; C07C 2523/62; B01J 23/62; B01J 23/626; B01J 35/08

See application file for complete search history.

(56) References Cited

U.S. PATENT DOCUMENTS

| | | |
|---|---|---|
| 4,430,517 A | 2/1984 | Imai et al. |
| 4,438,288 A | 3/1984 | Imai et al. |
| 4,677,237 A | 6/1987 | Imai et al. |
| 5,102,027 A | 4/1992 | Se Hong |
| 6,756,340 B2 | 6/2004 | Voskoboynikov et al. |
| 10,646,855 B2 * | 5/2020 | Serban .................. B01J 23/628 |
| 2006/0102520 A1 * | 5/2006 | Lapinski ................ C10G 35/09 208/138 |
| 2010/0331171 A1 | 12/2010 | Gajda et al. |

FOREIGN PATENT DOCUMENTS

| | | |
|---|---|---|
| CN | 104289218 A | 1/2015 |
| CN | 105709727 A | 6/2016 |
| CN | 106732574 A | 5/2017 |
| CN | 107899619 A | 4/2018 |
| CN | 108295846 A | 7/2018 |
| EP | 3375519 A1 | 9/2018 |
| WO | 2018097701 A2 | 6/2018 |

* cited by examiner

*Primary Examiner* — Sharon Pregler

(57) ABSTRACT

Catalysts and processes for a selective conversion of hydrocarbons. The catalyst comprises: a first component selected from the group consisting of Group VIII noble metals and mixtures thereof, a modifier selected from the group consisting of alkali metals or alkaline-earth metals and mixtures thereof, and a third component selected from the group consisting of tin, germanium, lead, indium, gallium, thallium and mixtures thereof; and a support forming a catalyst particle comprising a plurality of pores. The catalyst has a modifier profile index in a range of 1 to 1.4 across the catalyst particle.

14 Claims, No Drawings

DEHYDROGENATION CATALYST WITH OPTIMUM MODIFIER PROFILE INDEX

This application claims priority from provisional application 62/820,117, filed on Mar. 18, 2019.

BACKGROUND

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. A process for the conversion of paraffins to olefins involves passing a paraffin stream over a highly selective catalyst where the paraffin is dehydrogenated to the corresponding olefin. The dehydrogenation reaction is achieved under operating conditions selected to minimize the loss of feedstock. The typical process involves the use of a reactor (e.g., radial flow, fixed bed, fluidized bed, and the like) where a paraffin feedstock is contacted with a dehydrogenation catalyst under reaction conditions. One example of this process is the dehydrogenation of isobutane to produce isobutylene which can be polymerized to provide tackifying agents for adhesives, viscosity-index additives for motor oils, and impact-resistant and antioxidant additives for plastics. There is also a growing demand for isobutylene for the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al), U.S. Pat. No. 4,438,288 (Imai et al), and U.S. Pat. No. 6,756,340 (Voskoboynikov et al.) discuss a dehydrogenation process and catalyst for use therein. However, there remains an ongoing and continuous need for new catalytic material for selective hydrocarbon conversion processes, especially those that improve on one or more characteristics of the known catalytic compositions.

SUMMARY

A catalyst for a selective conversion of hydrocarbons is provided. The catalyst comprises a first component selected from the group consisting of Group VIII noble metals and mixtures thereof, a modifier selected from the group consisting of alkali metals or alkaline-earth metals and mixtures thereof, and a third component selected from the group consisting of tin, germanium, lead, indium, gallium, thallium and mixtures thereof; and a support forming a catalyst particle comprising a plurality of pores. The catalyst has a modifier profile index in a range of 1 to 1.4 across the catalyst particle. The catalyst may have a modifier profile index in a range of 1 to 1.2 or in a range of 1 to 1.1. The catalyst may comprise a first component that is platinum, a potassium modifier, and tin as the third component. The support may be silica, alumina, silica-alumina, a zeolite, a non-zeolitic molecular sieve, titania, zirconia or mixtures thereof. The catalyst particle may be spherical.

A process is provided for the selective conversion of hydrocarbons in which the process comprises contacting a hydrocarbon at selective conversion conditions with a catalytic composite comprising a first component selected from the group consisting of Group VIII noble metals and mixtures thereof, a modifier selected from the group consisting of alkali metals or alkaline-earth metals and mixtures thereof, a third component selected from the group consisting of tin, germanium, lead, indium, gallium, thallium and mixtures thereof, and a support forming a catalyst particle wherein the catalyst has a modifier profile index in a range of 1 to 1.4 across the catalyst particle. The process may produce more iso-butylene than a process using a catalyst having a modifier profile index greater than 1.4 and in some cases at least 1% more iso-butylene product than a process using a catalyst having a modifier profile index greater than 1.4 The process can produce less normal paraffin and olefin products than a process using a catalyst having a modifier profile index greater than 1.4 and in some cases at least 10% less normal paraffin and olefin products than a process using a catalyst having a modifier profile index greater than 1.4 The catalyst's modifier profile index may be in a range of 1 to 1.2 or 1 to 1.1.

In this process, the catalyst may have a first component that is platinum, a modifier that is potassium, and a third component that is tin. The support may be selected from silica, alumina, silica-alumina, a zeolite, a non-zeolitic molecular sieve, titania, zirconia and mixtures thereof. The catalyst particle may be spherical. The hydrocarbon may comprise at least one paraffin having 2 to 30 carbon atoms. The hydrocarbon may comprise at least one paraffin having 2 to 6 carbon atoms. The hydrocarbon may comprise at least one paraffin having 3 to 4 carbon atoms. The process may further comprise at least one of: sensing at least one parameter of the process and generating a signal or data from the sensing; generating and transmitting a signal; or generating and transmitting data.

DETAILED DESCRIPTION

Surprisingly, it was discovered that dehydrogenation catalysts have an optimum modifier profile index (MPI) in the relatively broad range of 1-1.4. Catalysts with MPI=1-1.4 make less coke in both propane and iso-butane dehydrogenation operations, are more selective towards iso-butylene, and make less undesired normal paraffin and olefin products in iso-butane operation. It is surprising that there seems to be an optimum range in MPI over a relatively broad range of 1-1.4, and not an optimum discrete MPI value. Surprisingly, for MPI>1.4, there seems to be a step change in iso-butylene selectivity and isomerization to normal paraffin and olefin products. The alumina support has Lewis acid sites active for isomerization reactions and acid cracking reactions. The role of the modifier is to quench the residual acidity and minimize and/or eliminate those undesired reactions. Without being bound by theory, it appears that an MPI in the range of 1-1.4 provides the catalyst with the desired modifier distribution across the catalyst pills. When the MPI is less than 1, or greater than 1.4, residual alumina acid sites located towards the edge, or the center of the catalyst pills, respectively, remain available for isomerization and cracking reactions.

The dehydrogenation catalyst with the modifier profile index in the range of 1 to 1.4 can be manufactured using several recipes. From a manufacturing point of view, it is advantageous that MPI is optimum over a relatively broad range, rather than an optimum discrete value close to 1, since this gives more flexibility in the impregnation and drying times used in the catalyst manufacturing. The catalyst can be used to maximize iso-butylene production and minimize isomerization to undesired linear paraffin and olefin products in iso-butane or mixed iso-butane, propane dehydrogenation operations.

One aspect of the invention is a catalyst for a selective conversion of hydrocarbons. In one embodiment, the catalyst comprises: a first component selected from the group consisting of Group VIII noble metals and mixtures thereof, a modifier selected from the group consisting of alkali metals or alkaline-earth metals and mixtures thereof, and a third component selected from the group consisting of tin, germanium, lead, indium, gallium, thallium and mixtures thereof; and a support forming a catalyst particle comprising a plurality of pores. The catalyst has a modifier profile index in a range of 1 to 1.4 across the catalyst particle.

The modifier profile index is calculated using Scanning Electron Microscope (SEM) Energy Dispersive Spectroscopy (EDS) analyses of at least 12 individual catalyst pills. The SEM metal concentration profiles are collected on a JEOL 7800 with Oxford Aztec EDS System using 30 kV accelerating voltage. Each point in the metal concentration profile is calculated using an average of analyzed points in the catalyst cross section, which are at a constant distance from the pill edge. This is done for a series of distances to produce the concentration profile. The MPI is then calculated from the profiles of all the catalyst pills analyzed. For example, for a 1.6 mm catalyst pill, the MPI is the ratio of the averaged modifier concentrations at the edge (arbitrarily defined as 0-200 microns) of all the catalyst pills analyzed and the averaged modifier concentrations at the center (arbitrarily defined as 500-700 microns) of all the catalyst pills analyzed.

In some embodiments, the modifier profile index is in a range of 1 to 1.2. In some embodiments, the modifier profile index in a range of 1 to 1.1.

In some embodiments, the first component is platinum, the modifier is potassium, and the third component is tin.

In some embodiments, the support is selected from the group consisting of silica, alumina, silica-alumina, a zeolite, a non-zeolitic molecular sieve, titania, zirconia and mixtures thereof.

In some embodiments, the catalyst particle is spherical.

Another aspect of the invention is a process for the selective conversion of hydrocarbons. In one embodiment, the process comprises: contacting a hydrocarbon at selective conversion conditions with a catalytic composite comprising a first component selected from the group consisting of Group VIII noble metals and mixtures thereof, a modifier selected from the group consisting of alkali metals or alkaline-earth metals and mixtures thereof, a third component selected from the group consisting of tin, germanium, lead, indium, gallium, thallium and mixtures thereof, and a support forming a catalyst particle, wherein the catalyst has a modifier profile index in a range of 1 to 1.4 across the catalyst particle.

In some embodiments, the process produces more iso-butylene than a process using a catalyst having a modifier profile index of greater than 1.4.

In some embodiments, the process produces at least 1% more iso-butylene than the process using the catalyst having the modifier profile index of greater than 1.4.

In some embodiments, the process produces less normal paraffin and olefin products than a process using a catalyst having a modifier profile index of greater than 1.4.

In some embodiments, the process produces at least 10% less normal paraffin and olefin products than a process using a catalyst having a modifier profile index of greater than 1.4.

In some embodiments, the modifier profile index in a range of 1 to 1.2. In some embodiments, the modifier profile index in a range of 1 to 1.1.

In some embodiments, the first component is platinum, the modifier is potassium, and the third component is tin.

In some embodiments, the support is selected from the group consisting of silica, alumina, silica-alumina, a zeolite, a non-zeolitic molecular sieve, titania, zirconia and mixtures thereof.

In some embodiments, the catalyst particle is spherical.

In some embodiments, the hydrocarbon comprises at least one paraffin having 2 to 30 carbon atoms. In some embodiments, the hydrocarbon comprises at least one paraffin having 2 to 6 carbon atoms. In some embodiments, the hydrocarbon comprises at least one paraffin having 3 to 4 carbon atoms.

In some embodiments, the process further comprises at least one of sensing at least one parameter of the process and generating a signal or data from the sensing; generating and transmitting a signal; or generating and transmitting data.

In one embodiment, the catalyst is a platinum, tin, potassium on spherical alumina porous support with an optimum MPI across the catalyst pills. In one embodiment, the catalyst can be used in the dehydrogenation of propane, iso-butane or mixed propane and iso-butane feeds.

Depending on the recipes used to manufacture the catalyst, the modifier profile across the catalyst pills can be either flat (MPI=1) or skewed, with higher modifier concentration at the edge of the pills. The MPI is calculated using the modifier concentrations measured via SEM-EDS analysis (Scanning Electron Microscopy Energy Dispersive Spectroscopy).

The dehydrogenation of paraffinic hydrocarbons is well known to those skilled in the art of hydrocarbon processing. Dehydrogenatable hydrocarbons are contacted with a dehydrogenation catalyst in a dehydrogenation zone maintained at dehydrogenation conditions. This contacting may be accomplished in a fixed catalyst bed system, a moving catalyst bed system, a fluidized bed system, etc., or in a batch-type operation. The dehydrogenation zone may comprise one or more separate reaction zones with heating means therebetween to ensure that the desired reaction temperature can be maintained at the entrance to each reaction zone. The hydrocarbon may be contacted with the catalyst bed in either upward, downward, or radial flow fashion. Radial flow of the hydrocarbon through the catalyst bed is preferred for a moving catalyst bed system. Radial flow reactors are constructed such that the reactor has an annular structure and annular distribution and collection devices. The devices for distribution and collection incorporate some type of screened surface. The screened surface is for holding catalyst beds in place and for aiding in the distribution of pressure over the surface of the reactor to facilitate radial flow through the reactor bed. The screen can be a mesh, either wire or other material, or a punched plate. For a moving bed, the screen or mesh provides a barrier to prevent the loss of solid catalyst particles while allowing fluid to flow through the bed. Solid catalyst particles are added at the top, flow through the apparatus, and are removed at the bottom, while passing through a screened-in enclosure that permits the flow of fluid over the catalyst. For example, the screens are described in U.S. Pat. Nos. 9,266,079 and 9,433,909 (Vetter et al.).

Hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 3 to 15 or more carbon atoms to the corresponding diolefins. The catalyst is especially useful in the dehydrogenation of $C_2$-$C_6$ paraffins, primarily propane, iso-butane, or mixtures of propane and iso-butane to monoolefins.

Dehydrogenation conditions include a temperature of from about 400° to about 900° C., a pressure of from about 0.01 to 10 atmospheres absolute, and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen, and the products of dehydrogenation reactions. This effluent stream is typically cooled, optionally compressed and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

In summary, a dehydrogenation process may include one or more dehydrogenation reactors, fired heaters, heat exchangers, quench towers, compressors, cryogenic separation systems, treatment systems, fuel gas preparation systems, light ends recovery systems, adsorption systems, fractionation columns, catalyst handling/regeneration equipment, as is known in the art and further discussed in "Handbook of Petroleum Refining Process, 4th Edition, Chapter 4.1."

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

EXAMPLE

Iso-Butane Dehydrogenation

In order to demonstrate the advantages to be achieved by the present invention, several dehydrogenation catalysts of same metal composition, but of varying MPIs were prepared and tested in a pilot plant. Each catalyst (15 $cm^3$) was tested for iso-butane dehydrogenation to produce iso-butylene for 26 hours on stream (HOS). The operating conditions of each pilot plant test included pure iso-butane feed, a hydrogen to feed ratio of 0.6, a liquid hourly space velocity (LHSV) of 11 $h^{-1}$, a pressure of 135 kPa (5 psig), a feed temperature of 645° C., and 70 ppm of hydrogen sulfide.

From Table 1 and FIGS. 1 and 2, it can be seen that the catalysts of the present invention with MPI=1-1.4 (Catalysts C, D and E) had higher selectivity to iso-butylene and lower isomerization to linear butane and butene compared to catalysts A and B.

TABLE 1

Selectivity to iso-butylene and isomerization to normal-butane and normal-butene at 55% iso-butane conversion

| CATALYST | MPI | Isobutylene Selectivity at 55% iC4 Conv.(%) | Isomerization at 55% iC4 Conv.(%) |
| --- | --- | --- | --- |
| CATALYST A | 1.8 | 87.3% | 3.5% |
| CATALYST B | 1.5 | 87.6% | 3.0% |
| CATALYST C | 1.4 | 88.6% | 2.2% |
| CATALYST D | 1.2 | 88.9% | 2.0% |
| CATALYST E | 1.1 | 89.0% | 2.0% |

Specific Embodiments

While the following is described in conjunction with specific embodiments, it will be understood that this description is intended to illustrate and not limit the scope of the preceding description and the appended claims.

A first embodiment of the invention is a catalyst for a selective conversion of hydrocarbons, the catalyst comprising a first component selected from the group consisting of Group VIII noble metals and mixtures thereof, a modifier selected from the group consisting of alkali metals or alkaline-earth metals and mixtures thereof, and a third component selected from the group consisting of tin, germanium, lead, indium, gallium, thallium and mixtures thereof; and a support forming a catalyst particle comprising a plurality of pores, wherein the catalyst has a modifier profile index in a range of 1 to 1.4 across the catalyst particle. An embodiment of the invention is one, any or all of prior embodiments in this paragraph up through the first embodiment in this paragraph wherein the modifier profile index is in a range of 1 to 1.2. An embodiment of the invention is one, any or all of prior embodiments in this paragraph up through the first embodiment in this paragraph wherein the modifier profile index is in a range of 1 to 1.1. An embodiment of the invention is one, any or all of prior embodiments in this paragraph up through the first embodiment in this paragraph wherein the first component is platinum, the modifier is potassium, and the third component is tin. An embodiment of the invention is one, any or all of prior embodiments in this paragraph up through the first embodiment in this paragraph wherein the support is selected from the group consisting of silica, alumina, silica-alumina, a zeolite, a non-zeolitic molecular sieve, titania, zirconia and mixtures thereof. The catalyst of claim 1 wherein the catalyst particle is spherical.

A second embodiment of the invention is a process for the selective conversion of hydrocarbons, the process comprising contacting a hydrocarbon at selective conversion conditions with a catalytic composite comprising a first component selected from the group consisting of Group VIII noble metals and mixtures thereof, a modifier selected from the group consisting of alkali metals or alkaline-earth metals and mixtures thereof, a third component selected from the group consisting of tin, germanium, lead, indium, gallium, thallium and mixtures thereof, and a support forming a catalyst particle, wherein the catalyst has a modifier profile index in a range of 1 to 1.4 across the catalyst particle. An embodiment of the invention is one, any or all of prior embodiments in this paragraph up through the second embodiment in this paragraph wherein the process produces more iso-butylene than a process using a catalyst having a modifier profile index greater than 1.4. An embodiment of the invention is one, any or all of prior embodiments in this paragraph up through the second embodiment in this paragraph wherein the process produces at least 1% more iso-butylene product than a process using a catalyst having a modifier profile index greater than 1.4. An embodiment of the invention is one, any or all of prior embodiments in this paragraph up through the second embodiment in this paragraph wherein the process produces less normal paraffin and olefin products than a process using a catalyst having a modifier profile index greater than 1.4. An embodiment of the invention is one, any or all of prior embodiments in this paragraph up through the second embodiment in this paragraph wherein the process produces at least 10% less normal paraffin and olefin products than a process using a catalyst having a modifier profile index greater than 1.4. An embodiment of the invention is one, any or all of prior embodiments in this paragraph up through the second embodiment in this paragraph wherein the modifier profile index in a range of 1 to 1.2. An embodiment of the invention is one, any or all of prior embodiments in this paragraph up through the second embodiment in this paragraph wherein the modifier profile index in a range of 1 to 1.1. An embodiment of the invention is one, any or all of prior embodiments in this paragraph up through the second embodiment in this paragraph wherein, the first component is platinum, the modifier is potassium, and the third component is tin. An embodiment of the invention is one, any or all of prior embodiments in this paragraph up through the second embodiment in this paragraph wherein the support is selected from the group consisting of silica, alumina, silica-alumina, a zeolite, a non-zeolitic molecular sieve, titania, zirconia and mixtures thereof. An embodiment of the invention is one, any or all of prior embodiments in this paragraph up through the second embodiment in this paragraph wherein the catalyst particle is spherical. An embodiment of the invention is one, any or all of prior embodiments in this paragraph up through the second embodiment in this paragraph wherein the hydrocarbon comprises at least one paraffin having 2 to 30 carbon atoms. An embodiment of the invention is one, any or all of prior embodiments in this paragraph up through the second embodiment in this paragraph wherein the hydrocarbon comprises at least one paraffin having 2 to 6 carbon atoms. An embodiment of the invention is one, any or all of prior embodiments in this paragraph up through the second embodiment in this paragraph wherein the hydrocarbon comprises at least one paraffin having 3 to 4 carbon atoms. An embodiment of the invention is one, any or all of prior embodiments in this paragraph up through the second embodiment in this paragraph, further comprising at least one of sensing at least one parameter of the process and generating a signal or data from the sensing; generating and transmitting a signal; or generating and transmitting data.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for the selective conversion of hydrocarbons, the process comprising:
   contacting a hydrocarbon at selective conversion conditions with a catalytic composite comprising
   a first component selected from the group consisting of Group VIII noble metals and mixtures thereof,
   a modifier selected from the group consisting of alkali metals or alkaline-earth metals and mixtures thereof,
   a third component selected from the group consisting of tin, germanium, lead, indium, gallium, thallium and mixtures thereof, and
   a support forming a catalyst particle,
   wherein the catalyst has a modifier profile index in a range of 1 to 1.4 across the catalyst particle.

2. The process of claim 1 wherein the process produces more iso-butylene than a process using a catalyst having a modifier profile index greater than 1.4.

3. The process of claim 1 wherein the process produces at least 1% more iso-butylene product than a process using a catalyst having a modifier profile index greater than 1.4.

4. The process of claim 1 wherein the process produces less normal paraffin and olefin products than a process using a catalyst having a modifier profile index greater than 1.4.

5. The process of claim 1 wherein the process produces at least 10% less normal paraffin and olefin products than a process using a catalyst having a modifier profile index greater than 1.4.

6. The process of claim 1 wherein the modifier profile index in a range of 1 to 1.2.

7. The process of claim 1 wherein the modifier profile index in a range of 1 to 1.1.

8. The process of claim 1 wherein, the first component is platinum, the modifier is potassium, and the third component is tin.

9. The process of claim 1 wherein the support is selected from the group consisting of silica, alumina, silica-alumina, a zeolite, a non-zeolitic molecular sieve, titania, zirconia and mixtures thereof.

10. The process of claim 1 wherein the catalyst particle is spherical.

11. The process of claim 1 wherein the hydrocarbon comprises at least one paraffin having 2 to 30 carbon atoms.

12. The process of claim 1 wherein the hydrocarbon comprises at least one paraffin having 2 to 6 carbon atoms.

13. The process of claim 1 wherein the hydrocarbon comprises at least one paraffin having 3 to 4 carbon atoms.

14. The process of claim 1, further comprising at least one of:
   sensing at least one parameter of the process and generating a signal or data from the sensing;
   generating and transmitting a signal; or
   generating and transmitting data.

* * * * *